(12) United States Patent
Thompson

(10) Patent No.: US 6,346,073 B1
(45) Date of Patent: Feb. 12, 2002

(54) IMAGING SYSTEM AND COMPONENTS THEREOF

(75) Inventor: Robert Lee Thompson, Rogers, AR (US)

(73) Assignee: Pinotage, LLC, Rogers, AK (US)

( * ) Notice: Subject to any disclaimer, the term of this patent is extended or adjusted under 35 U.S.C. 154(b) by 0 days.

(21) Appl. No.: 09/384,070

(22) Filed: Aug. 26, 1999

Related U.S. Application Data

(63) Continuation-in-part of application No. 09/064,452, filed on Apr. 22, 1998, now Pat. No. 5,980,450.
(60) Provisional application No. 60/045,817, filed on May 7, 1997, and provisional application No. 60/097,983, filed on Aug. 26, 1998.

(51) Int. Cl.[7] .................................. A61B 1/04
(52) U.S. Cl. .................. 600/112; 600/122; 600/167
(58) Field of Search .................. 600/112, 109, 600/122, 124, 133, 167; 348/73–75

(56) References Cited

U.S. PATENT DOCUMENTS

| | | | |
|---|---|---|---|
| 4,646,722 A | 3/1987 | Silverstein et al. | 128/4 |
| 4,736,733 A | 4/1988 | Adair | 128/6 |
| 4,741,326 A | 5/1988 | Sidall et al. | 128/4 |
| 4,878,113 A | 10/1989 | Nakamura | 358/98 |
| 4,914,521 A | 4/1990 | Adair | 358/229 |
| 4,947,827 A | 8/1990 | Opie et al. | 128/4 |
| 4,947,829 A | 8/1990 | Bullard | 128/11 |
| 5,131,380 A | 7/1992 | Heller et al. | 128/6 |
| RE34,110 E | 10/1992 | Opie et al. | 128/6 |
| 5,168,863 A | 12/1992 | Kurtzer | 128/4 |
| 5,188,093 A | 2/1993 | Lafferty et al. | 600/109 |
| 5,237,984 A | 8/1993 | Williams, III et al. | 128/4 |
| 5,239,981 A | 8/1993 | Anapliotis | 128/4 |
| 5,301,657 A | 4/1994 | Lafferty et al. | 128/6 |
| 5,334,150 A | 8/1994 | Kaali | 604/164 |
| 5,337,734 A | 8/1994 | Saab | 128/4 |
| 5,359,992 A | 11/1994 | Hori et al. | |
| 5,402,768 A | 4/1995 | Adair | 128/4 |
| 5,406,939 A | 4/1995 | Bala | 128/4 |
| 5,408,992 A | 4/1995 | Hamlin et al. | 128/4 |
| 5,431,150 A | 7/1995 | Yabe et al. | 600/121 |

(List continued on next page.)

FOREIGN PATENT DOCUMENTS

| | | | |
|---|---|---|---|
| DE | 89 14 215 | 2/1991 | |
| EP | 0 570 161 | 11/1993 | A61B/1/00 |
| GB | 2 148 526 | 5/1985 | |
| WO | WO 85/02101 | 5/1985 | |
| WO | WO 98/49929 | 11/1998 | |

Primary Examiner—John P. Leubecker
(74) Attorney, Agent, or Firm—Wolf, Greenfield & Sacks, P.C.

(57) ABSTRACT

In one embodiment, an imaging unit to be mated with an image-producing scope via a coupler includes at least one imaging unit body, and an image sensor disposed within the at least one imaging unit body. The imaging unit further includes a refractive lens movably disposed within the at least one imaging unit body, and at least one first component adapted to receive an output from a focusing mechanism disposed on a body of the coupler. The at least one first component is configured and arranged so that movement of the focusing mechanism with respect to the coupler body causes the lens to move within the at least one imaging unit body to focus an image produced by the scope onto the image sensor. In another embodiment, a method for operating an imaging system including an image-producing scope, a refractive lens, and an image sensor involves providing a coupler that is free of the refractive lens. According to the method, the coupler is disposed between the scope and the image sensor, and a focusing mechanism disposed on a body of the coupler is moved to cause a position of the refractive lens to be adjusted to focus an image produced by the scope onto the image sensor.

76 Claims, 5 Drawing Sheets

U.S. PATENT DOCUMENTS

| | | |
|---|---|---|
| 5,447,148 A | 9/1995 | Oneda et al. ................ 600/131 |
| 5,531,664 A | 7/1996 | Adachi et al. ............... 600/149 |
| 5,591,119 A | 1/1997 | Adair |
| 5,591,192 A | 1/1997 | Privitera et al. ............ 606/185 |
| 5,643,175 A | 7/1997 | Adair ......................... 600/133 |
| 5,702,349 A | 12/1997 | Morizumi |
| 5,792,045 A | 8/1998 | Adair |
| 5,876,328 A | 3/1999 | Fox et al. |
| 6,113,533 A * | 9/2000 | Howes et al. ................ 600/112 |

* cited by examiner

IMAGING SYSTEM AND COMPONENTS THEREOF

This application is a continuation-in-part of U.S. application Ser. No. 09/064,452, filed Apr. 22, 1998, now U.S. Pat. No. 5,980,450, which claims the benefit of U.S. Provisional Application No. 60/045,817, filed May 7, 1997. This application also claims the benefit of U.S. Provisional Application No. 60/097,983, filed Aug. 26, 1998.

BACKGROUND OF THE INVENTION

1. Field of the Invention

The present invention is directed to imaging systems including a camera and an image-producing scope.

2. Discussion of Related Art

An endoscope is a device, commonly used in the medical field, that may be used to view an interior cavity of a body. An endoscope typically includes an elongated shaft having a distal end to be inserted into a patient, and a proximal end having an eyepiece through which a user, such as a physician, may view the interior of the body cavity.

For some medical procedures, it is desirable to present an image of the interior of the body cavity on a display of an imaging system. For this purpose, it is known to use a coupling device to couple the eyepiece of an endoscope to an electronic image sensor of an imaging system so that the image sensor can sense the image produced by the endoscope and transmit an electronic signal representing the image to the imaging system display. The endoscope is typically sterilized prior to insertion into the patient. In addition, some technique is typically employed to ensure that the imaging system and the device for coupling it to the endoscope do not compromise the sterile environment.

FIG. 1 shows an example of such a prior art viewing system that includes four primary components: an endoscope 16 for insertion into the patient, an imaging unit 6 (connected to a monitor 46) for displaying an image within the patient's body cavity on the monitor, a coupling device 8 for coupling together the endoscope 16 and the imaging unit 6, and a sterile condom-like drape 5 which prevents the coupling device 8 and the imaging unit 6 from contaminating the sterile environment.

Endoscope 16 includes a distal end 13 which is adapted to be inserted into the patient (not shown) to view an object 9 within a body cavity of the patient. At its proximal end, the endoscope 16 includes an eyepiece 36 at which an image of the object 9 is presented. Imaging unit 6 includes housing 15 which houses an image sensor 14. The image sensor 14 senses an image along an imaging axis 17, and converts the sensed image into an electrical signal. This signal is passed, via a cable 26, to a monitor or display 46 which presents the sensed image to a user.

Coupling device 8 is used to couple together the eyepiece 36 of endoscope 16 and the housing 15, so that the imaging axis 17 of image sensor 14 passes through the eyepiece 36 and the length of the endoscope 16. In this manner, the image sensor 14 can sense the image of the object 9 within the patient. Coupling device 8 includes a refractive lens 20 which is movably mounted therein and a focusing mechanism 11 which may be manipulated to adjust a position of lens 20 within coupling device 8. When the coupling device 8 is mounted to the housing 15, lens 20 is aligned with the optical axis 17 of the image sensor 14 so that the optical axis 17 passes through the lens 20. By manipulating focusing mechanism 11, the focal length between the lens 20 and the image sensor 14 may be adjusted to focus the image (e.g., of object 9) that is presented at the eyepiece 36 on the image sensor 14.

The coupling device 8 and the housing 15 of the imaging unit 6 are typically not sterile. Therefore, the condom-like drape 5 is disposed between the eyepiece 36 and the coupling device 8 to prevent the non-sterile components from contaminating the sterile endoscope 16. Typically, the drape 5 is primarily formed from a flexible material that is not optically pure, and that would not convey a clear image from the eyepiece 36 to the image sensor 14. Thus, a window 7 of more optically pure material is typically provided in the drape 5. When the system is in use, the window 7 is aligned between the eyepiece 36 and the coupling device 8 so that the optical axis 17 of the image sensor 14 passes through the window 7.

SUMMARY OF THE INVENTION

According to one aspect of the present invention, an imaging unit is provided to be mated with an image-producing scope via a coupler. The imaging unit includes at least one imaging unit body, and an image sensor disposed within the at least one imaging unit body. The imaging unit further includes a refractive lens movably disposed within the at least one imaging unit body, and at least one first component adapted to receive an output from a focusing mechanism disposed on a body of the coupler. The at least one first component is configured and arranged so that movement of the focusing mechanism with respect to the coupler body causes the at least one first component to be moved with respect to the at least one imaging unit body, thereby causing the lens to move within the at least one imaging unit body to focus an image produced by the scope onto the image sensor.

According to another aspect of the invention, an imaging unit is provided to be mated with an image-producing scope via a coupler. The imaging unit includes at least one imaging unit body, and an image sensor disposed within the at least one imaging unit body. The imaging unit further includes a refractive lens movably disposed within the at least one imaging unit body, and means for receiving an output from a focusing mechanism disposed on a body of the coupler to move the lens within the at least one imaging unit body to focus an image produced by the scope onto the image sensor.

According to another aspect of the invention, an apparatus is provided for use in an imaging system including an image sensor, an image-producing scope, and a device having a refractive lens disposed therein. The apparatus includes a coupler body that is distinct from the device in which the lens is disposed. The apparatus further includes a focusing mechanism disposed on the coupler body such that adjustment of the focusing mechanism causes a position of the lens to be adjusted to focus an image produced by the scope onto the image sensor.

According to another aspect of the invention, an apparatus is provided for adapting a camera head for use in an imaging system including a coupler positioned between the camera head and an image-producing scope. The apparatus includes a housing adapted to mate with the camera head, and a refractive lens movably disposed within the housing. The apparatus further includes at least one first component adapted to receive an output from a focusing mechanism on a body of the coupler. The at least one first component is configured and arranged so that movement of the focusing mechanism with respect to the coupler body causes the at least one first component to be moved with respect to the housing, thereby causing the lens to move within the housing to focus an image produced by the scope onto the image sensor.

According to another aspect of the invention, an apparatus is provided for adapting a camera head for use in an imaging system including a coupler positioned between the camera head and an image-producing scope. The apparatus includes a housing adapted to mate with the camera head, and a refractive lens movably disposed within the housing. The apparatus further includes means for receiving an output from a focusing mechanism disposed on a body of the coupler to move the lens within the housing to focus an image produced by the scope onto the image sensor.

According to another aspect of the invention, a method for operating an imaging system including an image-producing scope, a refractive lens, and an image sensor involves providing a coupler that is free of the refractive lens. According to the method, the coupler is disposed between the scope and the image sensor, and a focusing mechanism disposed on a body of the coupler is moved to cause a position of the refractive lens to be adjusted to focus an image produced by the scope onto the image sensor.

DETAILED DESCRIPTION OF THE INVENTION

Figure 1:
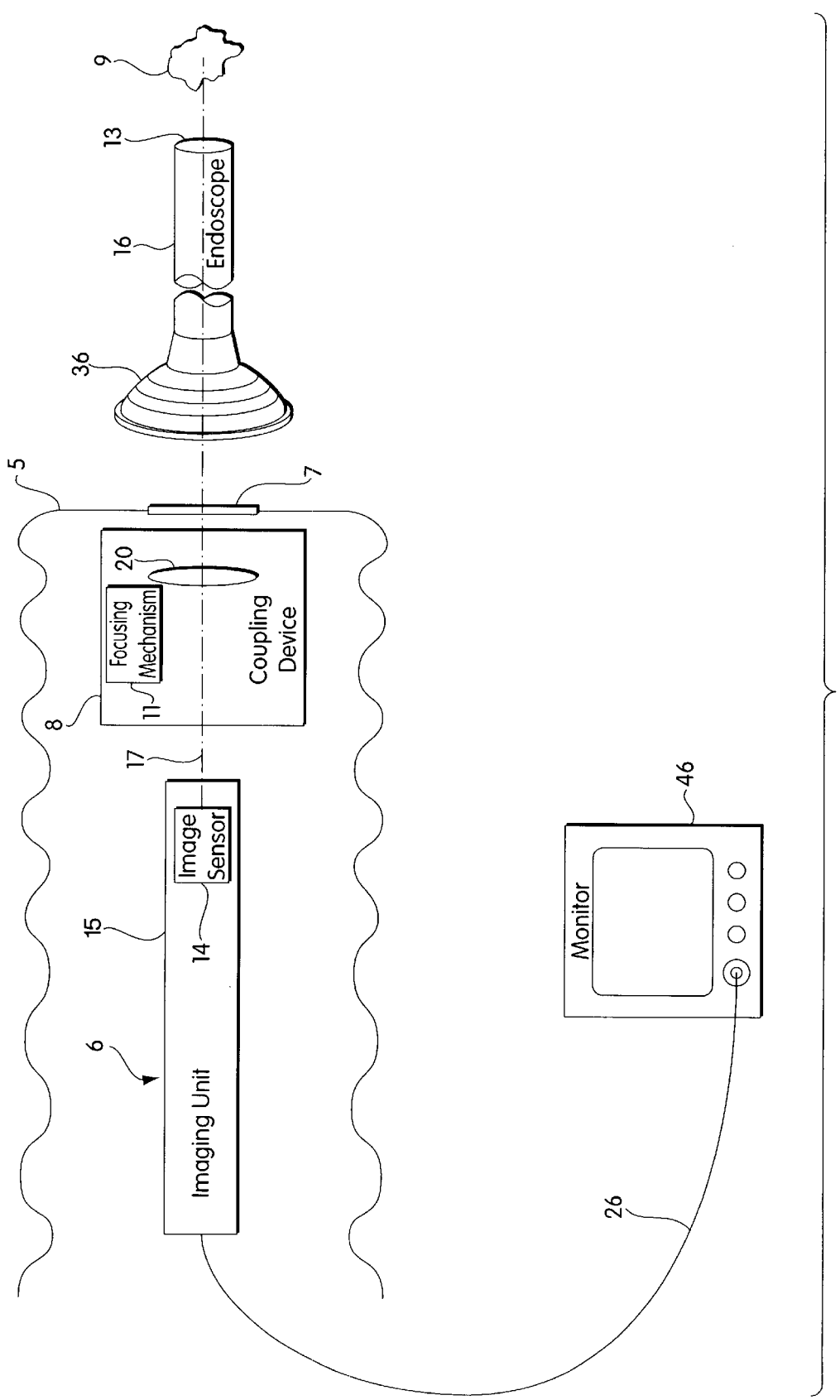
FIG. 1 is a schematic representation of a prior art imaging system that uses a coupler to interconnect an endoscope and an imaging unit.

Applicant has recognized numerous drawbacks of prior art coupling devices and the imaging systems in which they are used. A brief discussion of two of these drawbacks follows with reference to FIG. 1.

A first drawback is that the portion of the condom-like drape 5 that intersects the optical axis 17 of the image sensor 14 can interfere with the quality of the image generated on the monitor 46. The condom-like drape 5 is typically formed of pliable material that can wrinkle in front of lens 20, thereby causing the image generated by image sensor 14 to be distorted. Some prior art systems form the window 7 out of a stiffer material that is less likely to wrinkle. Nevertheless, it can be difficult to properly align the window 7 in front of the lens 20 when sandwiching the drape 5 between the endoscope 16 and the coupling device 8.

A second drawback is that the drape 5 is draped over the coupling device 8 and the focusing mechanism 11 located thereon. Thus, the user must manipulate the focusing mechanism 11 through the material of drape 5. This makes it difficult for the user to precisely adjust the focal length between the image sensor 14 and lens the 20 to achieve a sharp image on the monitor 46, and makes the drape 5 susceptible to tearing due to manipulation of the focusing mechanism.

Exemplary embodiments of the invention discussed below in connection with FIGS. 2–6 6 overcome each of the above-mentioned drawbacks. However, it should be appreciated that the present invention is not limited in this respect, and that alternate embodiments of the invention are contemplated that separately overcome either of these drawbacks. Furthermore, it should be understood that the illustrated embodiments of the present invention each also has numerous other advantages.

Figure 2:
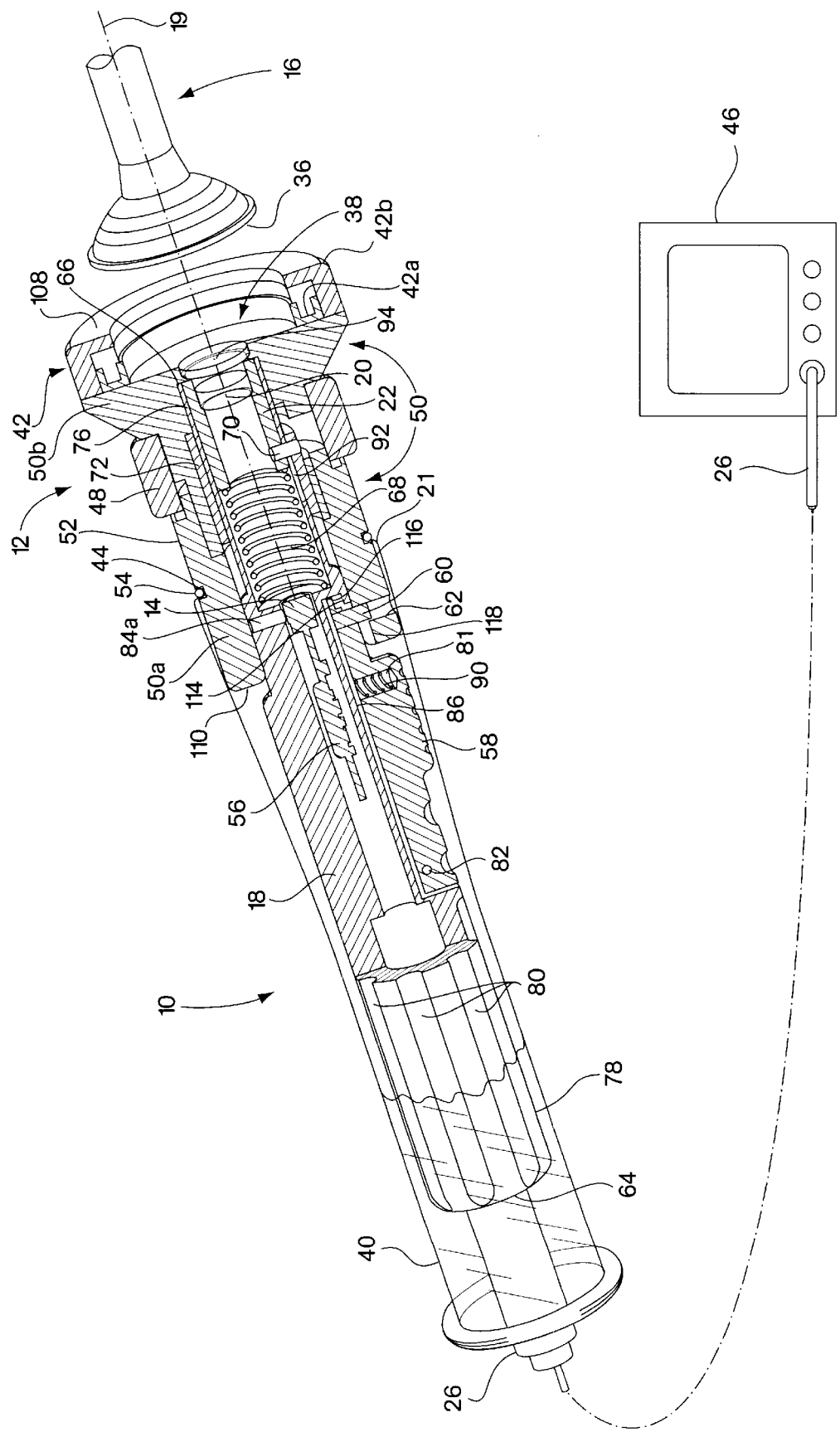
FIG. 2 is a partially cut away perspective view of a coupler and imaging unit according to one illustrative embodiment of the invention.

FIG. 2 is a partially cut away perspective view of an imaging system according to one embodiment of the invention. As shown, the imaging system includes four primary components, i.e., an endoscope 16, an imaging unit 10, a coupler 12, which couples the endoscope 16 to the imaging unit 10, and a condom-like drape 40, which prevents the imaging unit 10 from contaminating the sterile operating field. The imaging system can be employed with any type of image-producing scope, and is not limited to use with any particular type of scope.

As discussed in more detail below, in the exemplary imaging system shown in FIGS. 2–3, the condom-like drape 40 does not intercept the optical viewing axis of the system, thereby overcoming a number of the problems experienced in the prior art system of FIG. 1. In addition, the condom-like drape 40 does not cover a focusing mechanism 48 of the imaging system, making it easier to focus the system and lessening the likelihood that the drape 40 will be damaged due to manipulation of the focusing mechanism.

Figure 3:
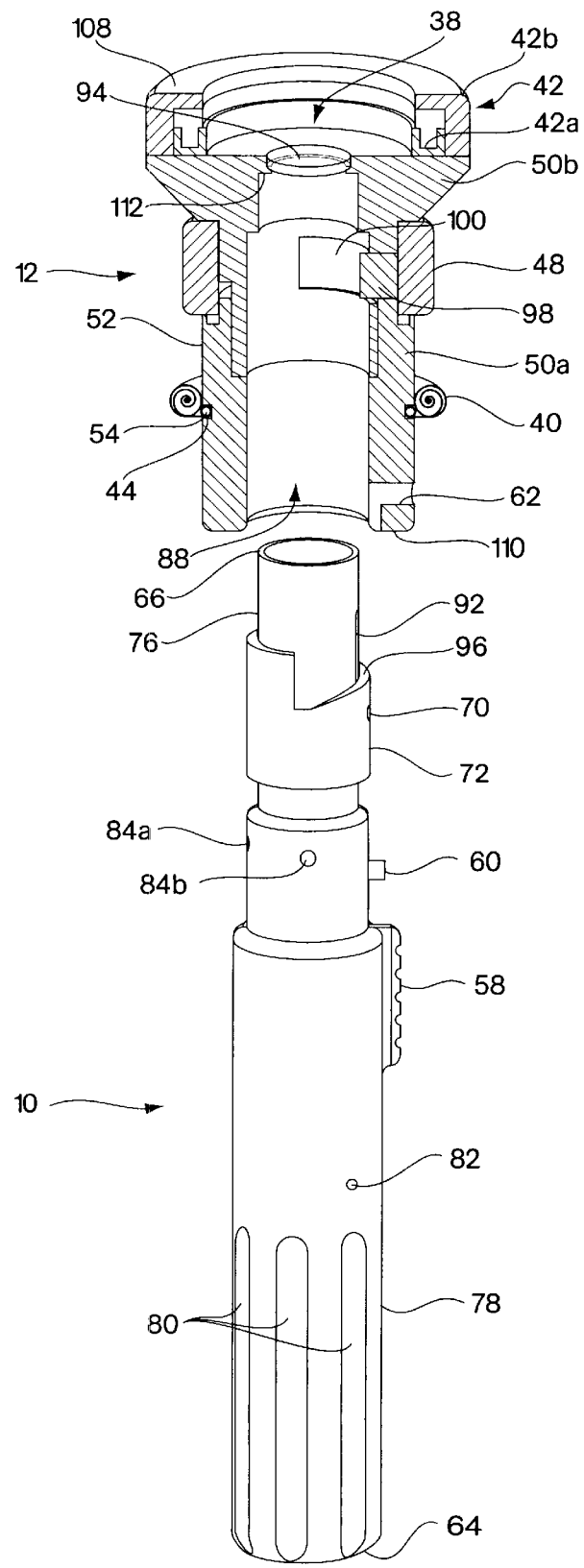
FIG. 3 is a partially cut away perspective view of the coupler and the imaging unit shown in FIG. 2.

Another significant difference between the embodiments of FIGS. 2–3 and the prior art system of FIG. 1 is that the lens for focusing the image from the endoscope to the imaging unit is provided in the imaging unit 10, rather than in the coupler 12. This is particularly advantageous because, as discussed in more detail below, in the exemplary embodiment shown, a portion of the coupler 12 is not separated from the endoscope 16 by the condom-like drape 40, and therefore, is sterile in use. By removing the refractive lens 20 from the coupler 12, the coupler 12 can be made significantly less expensively, thereby enabling the coupler 12 to be provided as a disposable part that need not be sterilized between uses. This is advantageous because the sterilization of the devices can be inconvenient and time consuming.

In the embodiment shown in FIGS. 2–3, the imaging unit 10 includes an image sensor 14 that is similar to that employed in the prior art system of FIG. 1, and that senses an image along an imaging axis (not shown). As with the prior art system of FIG. 1, when the imaging system is used, the coupler 12 is coupled between the eyepiece 36 of the endoscope 16 and a distal end 66 of the imaging unit 10 such that the lens 20 is disposed between the image sensor 14 and the eyepiece 36 to focus an image produced by the endoscope 16 onto the image sensor 14. However, in contrast to the prior art system of FIG. 1, the refractive lens 20 is provided in the imaging unit 10, rather than in the coupler 12. As discussed above, this is advantageous because the coupler can be made significantly less expensively, thereby enabling the coupler to be provided as a disposable part that need not be sterilized between uses.

The image sensor 14 may, for example, include a charge-coupled device (CCD) or a metal-oxide semiconductor (MOS) sensor. It should be appreciated, however, that the present invention is not limited in this respect, and can be employed with any type of image sensor 14. The image generated by the image sensor 14 can be conveyed to a monitor 46 in any of numerous ways, and the present invention is not limited to any particular implementation. For example, the image sensor 14 may be coupled to circuitry 56 which can assist in converting an image sensed by the image sensor 14 into an electrical signal. This electrical signal then may be transmitted (e.g., via cable 26) to the monitor 46 for display to a user or may be otherwise processed and/or recorded on a suitable medium. Alternatively, the image sensor 14 may comprise a bundle of fiber optic cables which optically transmit an image from the lens 20 to a viewing device for display to a user. Thus, the image sensor 14 need not necessarily convert the image from endoscope 16 into an electrical signal.

In the embodiment shown in FIG. 2, the imaging unit 10 is releasably mated with the coupler 12. This mating may be accomplished using any of a number of techniques, and the invention is not limited to any particular mating technique. FIGS. 2 and 3, however, illustrate one technique that may be used to mate these two components. In the particular embodiment shown, to mate imaging unit 10 with coupler 12, a distal end 66 of the imaging unit 10 is inserted into an opening 88 at a proximal end 110 of the coupler 12. As shown, the imaging unit 10 includes a button 58 which is pivotally connected, via a pin 82, to a body portion 18 of the imaging unit 10. The imaging unit 10 has a cavity 81 formed underneath the button 58 and a spring 90, disposed in the cavity 81. Spring 90 biases the button 58 (in a clockwise direction in FIG. 2) about pin 82 so that locking member 60 is biased away from a surface 86 of body portion 18. When a user pushes button 58 toward surface 86, however, spring 90 is compressed so that button 58 moves in a counterclockwise direction in FIG. 2 about pin 82 and locking member 60 moves toward surface 86. Thus, when the button 58 is depressed and the distal end 66 of the imaging unit is inserted into the opening 88 in the coupler 12, the locking member 60 moves toward surface 86 so that it can slide over edge 118 of the coupler 12. When the button 58 is released, the locking member 60 is biased (by spring 90) away from surface 86 and into a notch 62 in the coupler 12, and a shoulder 116 of imaging unit 10 contacts a shoulder 114 of the coupler 12, thereby interlocking the imaging unit 10 and the coupler 12. An indication that the distal end 66 of the imaging unit 10 is fully inserted into the opening 88 is provided by the distal end 66 contacting a shoulder 112 of coupler 12. The imaging unit 10 and coupler 12 can be separated by pushing button 58, which moves the locking member 60 out of the notch 62, and pulling the imaging unit 10 away from the coupler 12. As mentioned above, FIGS. 2–3 illustrate only one example of the many ways that the imaging unit 10 and coupler 12 may be mated together, and the present invention is not limited to this or any other particular implementation.

In the embodiment shown in FIGS. 2 and 3, the imaging unit 10 also includes a handle 78 proximal to the body portion 18. The handle 78 may include grooves 80 to make it easier for a user to grip the imaging unit 10 though the drape 40 that can be extended over the imaging unit 10 in a manner described below.

The image sensor 14 and circuitry 56 may be mounted in the body portion 18 of the imaging unit 10 in any of a number of ways. For example, the image sensor 14 may be mounted via pins or screws 84*a* and 84*b,* and circuitry 56 may be mounted on a circuit board supported within body portion 18. One or more wires (not shown) may be used to interconnect the circuitry 56 with the cable 26.

As discussed above, it is useful to enable the focal length between the image sensor 14 and the lens 20 of imaging unit 10 to be adjusted. In accordance with one exemplary embodiment of the invention, this can be accomplished via a mechanism that is not covered by the condom-like drape 40, thereby making it easier to focus the system and lessening the likelihood that the drape 40 will be damaged due to manipulation of the focusing mechanism. It should be appreciated, however, that the present invention is not limited in this respect, and that the focal length adjustment can be accomplished in any number of ways.

One example of a technique that is useful to perform the focal length adjustment is illustrated in FIGS. 2–4. In the embodiment shown, the refractive lens 20 is disposed in the imaging unit 10, rather than in the coupler 12. Thus, the focusing mechanism includes elements disposed in the imaging unit 10, as well as in the coupler 12. As mentioned above, placement of the lens 20 within the imaging unit 10, rather than in the coupler 12, provides at least one significant advantage. That is, according to such an embodiment, the cost of the coupler 12 may be reduced significantly below the cost of coupling devices that include lenses, thereby making it commercially practicable to use a new, sterile coupler each time the imaging system is used, rather than repeatedly sterilizing and reusing the same coupling device.

In the particular embodiment shown, the distal end 66 of the imaging unit 10 includes a primary cylinder 76, in which a spring 68 and a cylindrical lens holder 22 are disposed. Lens holder 22 supports the lens 20 in front of an imaging axis of image sensor 14. Lens holder 22 (and lens 20) can be moved within primary cylinder 76 either toward or away from distal end 66 of the imaging unit 10 so as to adjust the focal length between the image sensor 14 and the lens 20. Spring 68 biases lens holder 22 toward distal end 66. The position of lens holder 22 within primary cylinder 76 can be adjusted, however, through manipulation of a focusing mechanism on the coupler 12 as discussed below.

The imaging unit 10 further includes an outer cylinder 72, including a spirally ramped upper edge 96, which surrounds the primary cylinder 76. Outer cylinder 72 is movable with respect to primary cylinder 76 either toward or away from the distal end 66 of imaging unit 10. Outer cylinder 72 is connected to the lens holder 22 via a pin 70. Pin 70 extends through a slot 92 which extends a short distance along a length of the primary cylinder 76. Thus, in the embodiment shown, lens holder 22, outer cylinder 72 and pin 70 move as a single unit, with respect to primary cylinder 76, either toward or away from the distal end 66 of imaging unit 10. The manner in which this unit interacts with the focusing mechanism disposed on coupler 12 is described below in connection with FIGS. 4*a–b.*

FIGS. 2 and 3 show an exemplary embodiment of the coupler 12. The coupler 12 can be constructed in any of a number of ways to achieve the desired goal of enabling the imaging unit 10 to be coupled to the endoscope 16, and the present invention is not limited to the particular implementation shown in the figures. In the embodiment shown, the coupler 12 includes a main body 50 (including a proximal portion 50*a* and a distal portion 50*b*), a focusing ring 48, a light-penetrable window 94, a scope mounting portion 42 (including inner ring 42*a* and outer ring 42*b*) and the condom-like drape 40. The components constituting the main body 50, focusing ring 48 and scope-mounting portion 42 may be made of any suitable material and may be affixed together in any suitable manner. For example, they may be plastic molded components affixed together using an epoxy-based adhesive. For the embodiment of the invention wherein the coupler 12 is a disposable device, the coupler 12 is preferably formed from inexpensive components.

The main body 50 may be formed by inserting the distal portion 50b within the focusing ring 48, and then affixing together the proximal and distal portions 50a and 50b. Scope mounting portion 42 may be affixed to distal portion 50b. Main body 50 has an outer surface 52 between a distal end 108 and a proximal end 110 of the coupler 12. A channel 44 extends about a perimeter of the outer surface 52 between the focusing ring 48 and the proximal end 110.

When the coupler 12 is used in a medical application, it is generally important that the environment to which the patient is exposed remains sterile. It is also desirable, however, to not have to sterilize the imaging unit 10, thereby saving the time and expense of sterilization, and avoiding restrictions on the manner in which the imaging unit be formed, since it need not be sterilizable. Therefore, in accordance with one embodiment of the present invention, a sterile barrier is established between the sterile operating environment including the endoscope 16, and a non-sterile environment including the imaging unit 10. In one embodiment of the invention, such a sterile barrier is established by coupling the distal end 66 of the imaging, unit 10 to the coupler 12, and providing a hermetic seal between the components of the coupler 12 that separate the sterile and non-sterile environments. In the embodiment shown in the figures, a light-penetrable window 94 is hermetically sealed between the distal end 108 and the proximal end 110 of the coupler 12 to establish a sterile barrier therebetween. Window 94 may be made of glass, plastic, or any other suitable material through which light can pass from the endoscope 16 to the image sensor 14 (via lens 20) to generate a suitable image.

As mentioned above, the coupler 12 also includes the condom-like drape 40. The condom-like drape 40 may be made of any material that is suitable for creating a sterile barrier between a sterile environment and a non-sterile environment. For example, according to one embodiment, the condom-like drape may be made of a non-porous latex or plastic material. When the imaging unit 10 is mated with the coupler 12, the drape 40 may be extended to cover some or all of imaging unit 10 and cable 26 (FIG. 2). The condom-like drape 40 may be hermetically sealed to the outer surface 52 of coupler 12. It should be appreciated that in the embodiment shown in the figures, when each of the components of the coupler 12 is sterile, the hermetic seals between the main body portion 50 and the window 94 and drape 40 establish a sterile barrier between the endoscope 16 and the imaging unit 10, with the main body portion 50 of the coupler 12 itself forming a part of this sterile barrier. As compared to the prior art system shown in FIG. 1, in which a sterile barrier is formed only with the drape 5 and the window portion 7 thereof and in which the coupling device 8 is located entirely on the non-sterile side of this barrier, the embodiment shown in FIGS. 2–3 is superior because endoscope 16 can mate directly with body portion 50 rather than requiring the drape to be interposed between the coupling device and the endoscope as was done in the prior art. This feature therefore overcomes the drawbacks of the prior art system described above regarding the impact of the drape of the quality of the image produced by the system, and the difficulty of properly sandwiching the drape between the coupling device and the endoscope.

According to one embodiment of the present invention, the condom-like drape 40 does not intercept the optical viewing axis 19 of the imaging system. As mentioned above, this is advantageous in that the drape 40 need not be provided with a window that must be aligned with the optical viewing axis 19, and the drape 40 does not interfere with the quality of the image presented on the monitor 46. It should be appreciated that the function performed by the condom-like drape 40 can be achieved in any of numerous ways, and that the present invention is not limited to any particular implementation. For example, a protective drape can be provided that is more rigid than the condom-like drape 40 depicted in the drawings In the embodiment shown in the drawings, the condom-like drape 40 is substantially tubular in form and is open on its distal and proximal ends. The distal end 21 of the condom-like drape 40 is attached to the outer surface 52 (within channel 44) of the coupler 12. As discussed above, in one embodiment of the present invention, this attachment can be accomplished using a hermetic seal (e.g., via an O-ring 54) to maintain the separation between the sterile and non-sterile environments. The condom-like drape 40 can be provided in a rolled-up form attached to the coupler 12. After the coupler 12 is mated with to the imaging unit 10 as described above, the condom-like drape 40 can be unrolled to cover the non-sterile imaging unit 10. By encompassing the outer surface 52 of coupler 12 with the opening at the distal end 21 of the drape 40, the drape 40 can be used in conjunction with coupler 12 without requiring the user to align the drape 40, or a window portion thereof, between the eyepiece 36 of the endoscope 16 and the coupler 12, and without having the drape 40 intercept the optical viewing axis 19 of the imaging system.

FIGS. 2 and 3 illustrate one example of a technique that may be used to mate the endoscope 16 with the coupler 12. It should be appreciated that the invention is not limited in this respect, and that numerous other suitable mating techniques can be employed. In the embodiment shown in FIGS. 2 and 3, the endoscope 16 is mated with the coupler 12 by inserting the eyepiece 36 into an opening 38 at the distal end 108 of the coupler 12. Opening 38 may be formed by the inner and outer rings 42a–b of the scope mounting portion 42. In the embodiment shown, the inner and outer rings 42a–b form equal diameter openings, and inner ring 42a is movable with respect to outer ring 42b. A spring biases the inner ring 42a so that its center is forced to be offset from the center of the outer ring 42b unless a user activates a lever (not shown) to cause the centers of the two rings to align with one another.

To mate the endoscope 16 with the coupler 12, the user activates the lever so that the centers of the rings 42a–b align with one another and inserts the eyepiece 36 through both rings. The user then can release the lever so that the spring (not shown) causes the center of ring 42a to become offset from the center of ring 42b. Because the diameter of the eyepiece 36 is only slightly smaller than the diameter of each of rings 42a and 42b, when the centers of the rings are offset from one another, the eyepiece 36 will be locked within the scope mounting portion 42 of the coupler 12. The eyepiece 36 may be separated from the scope mounting portion 42 by pressing the lever to realign the centers of rings 42a and 42b and pulling the endoscope 16 away from the coupler 12.

In the embodiment of FIG. 2, the coupler 12 is shown as being mated directly with the eyepiece 36 of the endoscope 16. However, it should be appreciated that the invention is not limited in this respect, and that the endoscope 16 (or other image-producing scope) may alternatively be mated indirectly with the coupler 12. For example, the endoscope 16 may be mated with the coupler 12 via one or more additional coupling devices.

As discussed above, according to one embodiment of the invention, the user can directly manipulate a focusing mechanism without having to do so through a portion of a protective drape such as condom-like drape 40. The present invention is not limited to use with any particular type of focusing mechanism, as any mechanism can be employed that serves to adjust the focal length between the lens 20 and image sensor 14 in the imaging unit 10. In the exemplary embodiment of the invention shown in FIGS. 2–4, a focusing ring 48 is provided on the coupler 12 to perform this focal length adjustment. The focusing ring 48 is disposed distally of the distal end 21 of the condom-like drape 40, so that after the drape 40 is extended to cover some or all of the imaging unit 10 and cable 26 (FIG. 2), the focusing ring 48 is not covered by the drape 40 and may be manipulated by a user to adjust the focal length between the lens 20 and the image sensor 14 without also having to manipulate the drape 40. Hence, this feature makes focusing ring 48 relatively easy for the user to manipulate to achieve sharp focusing, and reduces the risk of damage to drape 40.

Figure 4A:
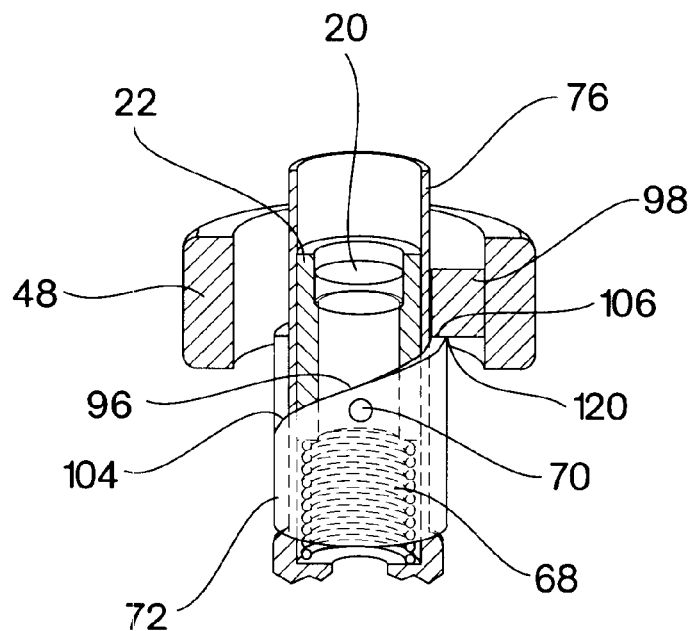
FIGS. 4a and 4b are partially cut away perspective views of an illustrative focusing mechanism employed in the system of FIGS. 2–3.
Figure 4B:
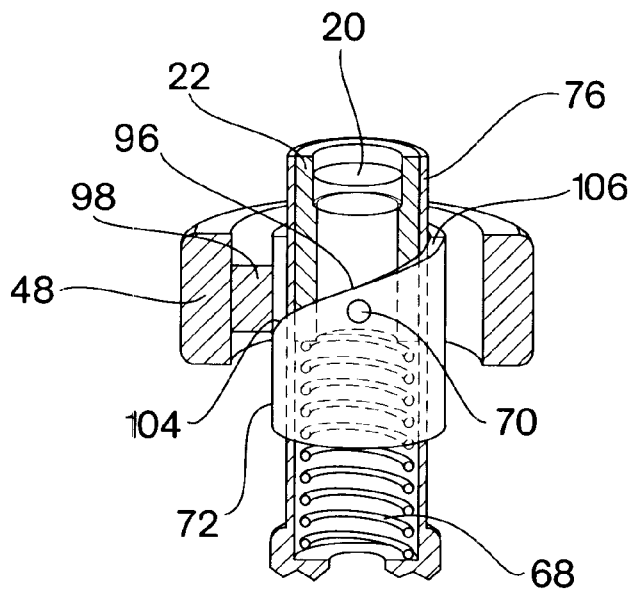

An illustrative example of a linkage assembly for mechanically coupling the focusing ring 48 on the coupler 12 to the imaging unit 10 to adjust the focal length between the lens 20 and image sensor 14 is shown in FIGS. 3 and 4*a*–*b*. It should be appreciated that the present invention is not limited to this particular linkage assembly, as numerous other implementations are possible. In the embodiment shown, the distal portion 50*b* of the main body portion 50 of coupler 12 has an annular groove 100. Annular groove 100 may be covered by the focusing ring 48, so that it is not visible from the outside of coupler 12. A finger 98 extends inwardly from the focusing ring 48 through the annular groove 100, so that when the focusing ring 48 is rotated about the main body portion 50, finger 98 slides within the annular groove 100.

As shown in FIGS. 4*a*–*b*, when the imaging unit 10 is mated with the coupler 12, a lower surface 120 of finger 98 contacts a portion of a spiraling ramp surface 96 on the outer cylinder 72. As mentioned above, pin 70 may be connected between the outer cylinder 72 and the cylindrical lens holder 22 through the slot 92, which extends along the length of the primary cylinder 76, so that the outer cylinder 72 and lens holder 22 do not rotate with respect to the primary cylinder 76. The focusing ring 48, however, can rotate freely about the primary cylinder 76, limited only by the movement of the finger 98 within the annular groove 100.

As the focusing ring 48 rotates with respect to the primary cylinder 76, a bottom surface 120 of the finger 98 slides along the spiraling ramped surface 96. The spring 68 pushes upwardly on outer cylinder 72 to keep a portion of the spiraling ramped upper surface 96 in contact with bottom surface 120 of the finger 98 at all times. Enough friction exists between the focusing ring 48 and the main body 50 of the coupler 12 to prevent the spring 68 from rotating the focusing ring 48 when it is not being manipulated by a user. This friction makes the fine tuning of the focal length between the lens 20 and image sensor 14 (using focusing ring 48) relatively easy to accomplish.

FIGS. 4*a* and 4*b* illustrate the focusing mechanism at its two extreme focusing positions, with FIG. 4*a* illustrating the lens 20 at its closest position to the image sensor 14 and FIG. 4*b* illustrating the lens 20 at its furthest position from the image sensor 14. As shown in FIG. 4*a*, when the lens 20 is at its closest position to the image sensor 14, the spring 68 is fully compressed, bottom surface 120 of finger 98 is in contact with a point 106 near the top of the spiraling ramped surface 96, and the finger 98 is in a first position with respect to the primary cylinder 76. In contrast, as shown in FIG. 4*b*, when the lens 20 is at its furthest position from the image sensor 14, the spring 68 is fully extended, the bottom surface 120 of finger 98 is in contact with a point 104 near the bottom of the spiraling ramped surface 96, and the finger 98 is in a second position with respect to the primary cylinder 76, which is on an opposite side from the first position (FIG. 4*a*).

It should be appreciated that the present invention is not limited to the above-described system for adjusting the focal length between the image sensor 14 and the lens 20. This implementation is only one example of the many possible systems that can achieve this result, as other implementations can alternatively be employed.

Figure 5:
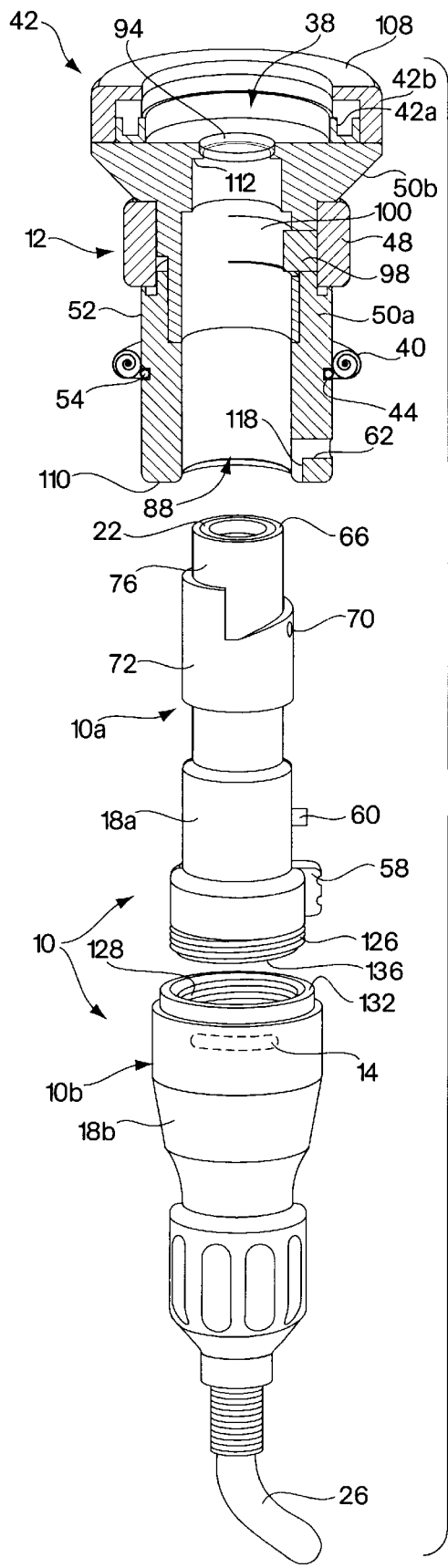
FIG. 5 is a partially cut away perspective view of an alternative embodiment of the invention directed to an imaging system including an adaptor that adapts a standard camera head to be mated with the coupler shown in FIGS. 2–3.
Figure 6:
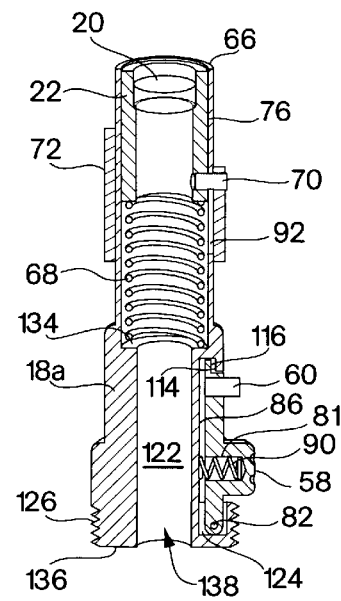
FIG. 6 is a partially cut away perspective view of the adaptor shown in FIG. 5.

In the illustrative embodiment of FIGS. 2–3, the imaging unit 10 includes a single body portion 18 in which both the image sensor 14 (and associated circuitry 56) and the refractive lens 20 (and associated components such as the lens holder 22, the spring 68, and the cylinders 72 and 76) are disposed. It should be appreciated, however, that the invention is not limited in this respect, as various components of the imaging unit 10 may alternatively be distributed among two or more separate housings that may be mated together to form the imaging unit 10. An illustrative example of an imaging system configured in this manner is shown in FIGS. 5 and 6. As shown in FIG. 5, the imaging unit 10 to be mated with the coupler 12 may include a first housing 18*a* in which the refractive lens (and associated components) is disposed, and a second housing 18*b* in which the image sensor 14 (and associated circuitry (not shown)) is disposed.

In the illustrative embodiment shown in FIGS. 5–6, the second housing 18*b* is the housing of a camera head 10*b* (e.g., a standard C-mount camera head), and the first housing 18*a* is the housing of an adaptor 10*a* for adapting the camera head 10*b* for use with the coupler 12. When the adaptor 10*a* is mated with the camera head 10*b* (as discussed below), the adaptor 10*a* and the camera head 10*b* together form a composite imaging unit 10 which is similar to the imaging unit 10 described above in connection with FIGS. 2–3. Although the example shown in FIGS. 5–6 includes a C-mount camera head and adaptor therefor, it should be appreciated that the invention is not limited in this respect, as each of the housings 18*a*–*b* may take on any of a number of alternative forms. For example, the housing 18*b* may alternatively be the housing of a standard V-mount camera head, or any other device in which an image sensor is disposed, and the housing 18*a*, may be configured to be mated with the same.

It should also be appreciated that the imaging unit 10 may further include additional housings, and the invention is not limited to configurations including only one or two housings. For example, referring to the FIG. 5 embodiment, the imaging unit 10 may further include one or more housings disposed between the housings 18*a* and 18*b* or between the housing 18*a* and the coupler 12. Such an additional housing may exist, for example, in the form of a coupling device that couples together the housings 18*a* and 18*b* or the housing 18*a* and the coupler 12. It should be appreciated that the imaging unit actually employed may be any of numerous devices or combinations of devices capable of receiving an optical image along an imaging axis, and that the invention is not limited to any particular type of imaging unit. As used herein, the term "imaging unit" is not intended to be limiting. Rather, it is intended to refer to any device or combination of devices capable of performing an imaging function.

Further, while in the embodiments of FIGS. 2–5 the coupler 12 is shown as being mated directly with the distal end 66 of the imaging unit 10, it should be appreciated that the invention is not limited in this respect, and that the imaging unit 10 may alternatively be mated indirectly with the coupler 12. For example, the imaging unit 10, in whatever form, may be mated with the coupler 12 via one or more additional coupling devices.

In the illustrative embodiment shown in FIGS. 5–6, the operational interface between the adaptor 10a and the coupler 12 is identical in most respects to the operational interface between the imaging unit 10 and the coupler 12 described above in connection with the embodiment of FIGS. 2–4. Corresponding components in the two embodiments have therefore been labeled with identical reference numerals, and reference may be made to the description of the embodiment of FIGS. 2–4 for an in-depth understanding of the operational interface between the adaptor 10a and the coupler 12 of the embodiment of FIGS. 5–6.

As mentioned above, the camera head 10b may, for example, be a standard C-mount camera head. Therefore, as shown in FIG. 5, the camera head 10b may include a threaded, female connector 128 formed at a distal end 132 thereof. To permit the adaptor 10a to mate with the connector 128 of the camera head 10b, the adaptor 10a may include a threaded, male connector 126 formed at a proximal end 136 thereof.

As shown in FIG. 5, the image sensor 14 may be disposed adjacent the distal end 132 of the camera head 10b so that, when the male connector 126 of the adaptor 10a is threaded into the female connector 128 of the camera head 10b, the image sensor 14 is disposed adjacent an opening 138 at the proximal end 136 of the adaptor 10a. In the embodiment of FIGS. 5–6, the image sensor 14 is therefore disposed further from the distal end 66 of the imaging unit 10 than it is in the embodiment of FIGS. 2–3. For this reason, in the embodiment of FIGS. 5–6, an annular cavity 122 is formed within the housing 18a to provide an optical pathway between the refractive lens 20 and the image sensor 14 along which an image produced by the endoscope 16 (FIG. 2) can be focused onto the image sensor 14 via the lens 20. The cavity 122 may be formed, for example, by reducing a width of an annular shoulder 134 (FIG. 6) supporting one end of the spring 68 to be narrower than in the embodiment of FIGS. 2–3.

In addition, in the embodiment of FIGS. 5–6, the button 58 is disposed on the adaptor 10a of the imaging unit 10, and is therefore disposed distally of the image sensor 14 in this embodiment, rather than proximally of the image sensor 14 as in the embodiment of FIGS. 2–3.

As shown, to make the button 58 fit on the adaptor 10a, the button 58 may be shortened as compared to the embodiment of FIGS. 2–4. Additionally, the pin 82 about which the button 58 pivots may be disposed within a small cavity 124 adjacent the proximal end 136 of the adaptor 10a, rather than being disposed proximally of the image sensor 14 as in the embodiment of FIGS. 2–4. It should be appreciated, of course, that the button 58 and locking member 60 represent only one example of numerous mechanisms that can be used to interconnect the imaging, unit 10 with the coupler 12, and that the imaging unit 10 may be mated with the coupler 12 in different ways in alternative embodiments of the invention. In such alternative embodiments, the imaging unit 10 may not include a button such as the button 58 or a locking member such as the locking member 60 at all, and may instead provide a different mechanism for mating the imaging unit 10 with the coupler 12.

In light of the above description, it should be appreciated that, as far as the physical interface between the imaging unit 10 and the coupler 12 is concerned, the imaging unit 10 that is formed when the adaptor 10a is mated with the camera head 10b can be made identical in all respects to the imaging unit 10 of embodiment of FIGS. 2–4. Additionally, by properly adjusting the refractive index of the lens 20 to account for the increased distance between the distal end 66 and the image sensor 14 in the embodiment of FIGS. 5–6 as compared to the embodiment of FIGS. 2–4, the imaging unit 10 of FIGS. 5–6 can also be made to mimic the functional characteristics of the imaging unit 10 of FIGS. 2–4 as well. The use of the adaptor 10a of FIGS. 5–6 therefore enables a standard camera head (e.g., the camera head 10b ) to be adapted for use with the inventive coupler 12 described herein in the same manner as in the embodiment of the imaging unit 10 described in connection with FIGS. 2–4. Therefore, one already in possession of a camera head 10b (e.g., a standard C-mount or V-mount camera head) may simply purchase the adaptor 10a (which does not include an image sensor) for use with the coupler 12, rather than purchasing the imaging unit 10 of FIGS. 2–4 (which additionally includes an image sensor) for use therewith.

The embodiment of the adapter 10a described herein is configured for use with a specific type of coupler (i.e., the coupler 12). However, it should be appreciated that the adaptor 10a may alternatively be configured for use with other types of devices or couplers, and that the invention is not limited to an adaptor configured for use with the particular coupler shown.

Having thus described at least one illustrative embodiment of the invention, various alterations, modifications and improvements will readily occur to those skilled in the art. Such alterations, modifications and improvements are intended to be within the spirit and scope of the invention. Accordingly, the foregoing description is by way of example only and is not intended as limiting. The invention is limited only as defined in the following claims and the equivalents thereto.

What is claimed is:

1. An imaging unit to be mated with a proximal end of an image-producing scope via a coupler including a coupler body having first and second ends and a focusing, mechanism disposed thereon, wherein the first end of the coupler body is attachable to the proximal end of the scope and the second end of the coupler body is attachable to the imaging unit, the imaging unit comprising:

at least one imaging unit body having a distal end;

an image sensor disposed within the at least one imaging unit body;

a refractive lens movably disposed within the at least one imaging unit body to focus an image produced by the scope onto the image sensor; and at least one first component movably attached to the at least one imaging unit body and adapted to receive an output from the focusing mechanism on the coupler body, the at least one first component being mechanically coupled to the lens and configured and arranged so that movement of the focusing mechanism with respect to the coupler body causes the at least one first component to be moved with respect to the at least one imaging unit body, thereby causing the lens to move within the at least one imaging unit body to focus the image produced by the scope onto the image sensor.

2. The imaging unit of claim 1, in combination with the coupler.

3. The combination of claim 2, wherein the scope includes an endoscope, and wherein the first end of the coupler is adapted to releasably mate with an eyepiece of the endoscope.

4. The combination of claim 2, wherein the coupler includes a sterile drape that is extendible to accommodate at least a portion of the imaging unit when the imaging unit and coupler are mated together.

5. The combination of claim 4, wherein the drape is hermetically sealed to the coupler.

6. The combination of claim 2, wherein the coupler includes a sterile drape, wherein the coupler body has an outer surface, and wherein the drape has an opening mounted about the outer surface of the coupler body.

7. The combination of claim 6, wherein the drape is hermetically sealed to the coupler body.

8. The combination of claim 2, wherein the opening of the drape is mounted on the coupler body proximally of the focusing mechanism.

9. The combination of claim 8, wherein:
the focusing mechanism includes a second component; and
the at least one first component is configured and arranged such that adjustment of the focusing mechanism causes the second component to bear against the at least one first component, thereby moving the at least one first component with respect to the at least one imaging unit body and causing the lens to move within the at least one imaging unit body to focus the image produced by the scope onto the image sensor.

10. The combination of claim 9, wherein:
the focusing mechanism includes a focusing ring rotatably disposed on the coupler body;
the second component includes a finger extending from the focusing ring that rotates in a plane perpendicular to an imaging axis extending between the scope and the image sensor;
the at least one first component includes a lens holder, having the lens disposed therein, slidingly disposed within the at least one imaging unit body, and an outer cylinder slidingly disposed about the at least one imaging unit body so that the outer cylinder outer cylinder is prohibited from rotating in the plane perpendicular to the imaging axis but is permitted to slide in along the imaging axis, the outer cylinder being mechanically coupled to the lens holder so that sliding the outer cylinder along the imaging axis causes the lens holder to slide along the imaging axis, thereby causing the lens to move along the imaging axis to focus the image produced by the scope onto the image sensor, the outer cylinder having a ramped surface disposed at an end thereof that is angled with respect to the plane perpendicular to the imaging axis; and
the outer cylinder and the finger are configured and arranged such that rotation of focusing mechanism about the coupler body causes the finger to bear against and slide along the ramped surface so that the outer cylinder slides along the imaging axis and moves the lens holder and the lens within the at least one imaging unit body to focus the image produced by the scope onto the image sensor.

11. The combination of claim 2, wherein the focusing mechanism is sterile.

12. The combination of claim 2, wherein the first and second ends of the coupler body are respectively adapted to releasable mate with the distal end of the at least one imaging unit body and the proximal end of the scope.

13. The combination of claim 2, in combination with the scope.

14. The imaging unit of claim 1, wherein the at least one first component is configured and arranged such that the focusing mechanism slid ably engages the at least one first component so that movement of the focusing mechanism with respect to the coupler body causes the at least one first component to move with respect to the at least one imaging unit body to focus the image produced by the scope onto the image sensor.

15. The imaging unit of claim 1, wherein the focusing mechanism includes a second component, and wherein:
the at least one first component is configured and arranged such that adjustment of the focusing mechanism causes the second component to bear against the at least one first component, thereby moving the at least one first component with respect to the at least one imaging unit body and causing the lens to move within the at least one imaging unit body to focus the image produced by the scope onto the image sensor.

16. The imaging unit of claim 15, wherein the focusing mechanism includes a focusing ring rotatably disposed on the coupler body, wherein the second component includes a finger extending from the focusing ring that rotates in a plane perpendicular to an imaging axis extending between the scope and the image sensor, and wherein:
the at least one first component includes a lens holder, having the lens disposed therein, slidingly disposed within the at least one imaging unit body, and an outer cylinder slidingly disposed about the at least one imaging unit body so that the outer cylinder is prohibited from rotating in the plane perpendicular to the imaging axis but is permitted to slide along the imaging axis, the outer cylinder being mechanically coupled to the lens holder so that sliding the outer cylinder along the imaging axis causes the lens holder to slide along the imaging axis, thereby causing the lens to move along the imaging axis to focus the image produced by the scope onto the image sensor, the outer cylinder having a ramped surface disposed at an end thereof that is angled with respect to the plane perpendicular to the imaging axis; and
the finger is configured and arranged such that rotation of focusing mechanism about the coupler body causes the finger to bear against and slide along the ramped surface so that the outer cylinder slides along the imaging axis and moves the lens holder and the lens within the at least one imaging unit body to focus the image produced by the scope onto the image sensor.

17. The imaging unit of claim 1, wherein the at least one first component includes means for receiving an output from the focusing mechanism on the coupler body to move the lens within the at least one imaging unit body to focus the image produced at the proximal end of the scope onto the image sensor.

18. The imaging unit of claim 1, wherein:
the at least one imaging unit body includes first and second separate housings;
the image sensor is disposed within the first housing;
the lens is disposed within the second housing; and
the first housing is adapted to releasable mate with the second housing.

19. The imaging unit of claim 18, wherein each of the first and second housings includes a connector selected from a group consisting of a C-mount connector and a V-mount connector.

20. The imaging unit of claim 19, wherein the connector of the first housing is a female connector and the connector of the second housing is a male connector.

21. The imaging unit of claim 1, wherein the at least one imaging unit body includes means for mating the at least one imaging unit body with the coupler body.

22. The imaging unit of claim 1, wherein the at least one first component is configured and arranged so that movement of the focusing mechanism with respect to the coupler body, while maintaining a fixed relationship between the coupler body and the at least one imaging unit body, causes the at least one first component to be moved with respect to the at least one imaging unit body, thereby causing the lens to move within the at least one imaging unit body to focus the image produced by the scope onto the image sensor.

23. An imaging unit to be mated with a proximal end of an image-producing scope via a coupler including a coupler body having a first and second ends and a focusing mechanism disposed thereon, wherein the first end of the coupler body is attachable to the proximal end of the scope and the second end of the coupler body is attachable to the imaging unit, the imaging unit comprising:

at least one imaging unit body having a distal end;

an image sensor disposed within the at least one imaging unit body;

a refractive lens movably disposed within the at least one imaging unit body to focus an image produced by the scope onto the image sensor; and means for receiving an output from the focusing mechanism on the coupler body to move the lens within the at least one imaging unit body to focus the image produced by the scope onto the image sensor.

24. The imaging unit of claim 23, in combination with the coupler.

25. The combination of claim 24, in combination with the scope.

26. The imaging unit of claim 23, wherein:

the at least one imaging unit body includes first and second separate housings;

the image sensor is disposed within the first housing;

the lens is disposed within the second housing; and the first housing is adapted to releasable mate with the second housing.

27. The imaging unit of claim 26, wherein each of the first and second housings includes a connector selected from a group consisting of a C-mount connector and a V-mount connector.

28. The imaging unit of claim 27, wherein the connector of the first housing is a female connector and the connector of the second housing is a male connector.

29. The imaging unit of claim 23, wherein the at least one imaging unit body includes means for mating the at least one imaging unit body with the coupler body.

30. The imaging unit of claim 23, wherein the means for receiving includes means for receiving the output from the focusing mechanism on the coupler body while maintaining a fixed relationship between the coupler body and the at least one imaging unit body.

31. An apparatus for adapting a camera head for use in an imaging system including the camera head and a coupler positioned between the camera head and an image-producing scope, the camera head including an image sensor, the coupler including a coupler body and a focusing mechanism disposed thereon to focus an image produced by the scope onto the image sensor, the apparatus comprising:

a housing adapted to mate with the camera head;

a refractive lens movably disposed within the housing to focus an image produced by the scope onto the image sensor; and at least one first component movably attached to the housing and adapted to receive an output from the focusing mechanism on the coupler body, the at least one first component being mechanically coupled to the lens and configured and arranged so that movement of the focusing mechanism with respect to the coupler body causes the at least one first component to be moved with respect to the housing, thereby causing the lens to move within the housing to focus the image produced by the scope onto the image sensor.

32. The apparatus of claim 31, in combination with the coupler.

33. The combination of claim 32, wherein:

the focusing mechanism includes a second component; and the at least one first component is configured and arranged such that adjustment of the focusing mechanism causes the second component to bear against the at least one first component, thereby moving the at least one first component with respect to the housing and causing the lens to move within the housing to focus the image produced by the scope onto the image sensor.

34. The combination of claim 33, wherein:

the focusing mechanism includes a focusing ring rotatably disposed on the coupler body;

the second component includes a finger extending from the focusing ring that rotates in a plane perpendicular to an imaging axis extending between the scope and the image sensor;

the at least one first component includes a lens holder, having the lens disposed therein, slidingly disposed within the housing, and an outer cylinder slidingly disposed about the housing so that the outer cylinder outer cylinder is prohibited from rotating in the plane perpendicular to the imaging axis but is permitted to slide along the imaging axis, the outer cylinder being mechanically coupled to the lens holder so that sliding the outer cylinder along the imaging axis causes the lens holder to slide along the imaging axis, thereby causing the lens to move along the imaging axis to focus the image produced by the scope onto the image sensor, the outer cylinder having a ramped surface disposed at an end thereof that is angled with respect to the plane perpendicular to the imaging axis; and the outer cylinder and the finger are configured and arranged such that rotation of focusing mechanism about the coupler body causes the finger to bear against and slide along the ramped surface so that the outer cylinder slides along the imaging axis and moves the lens holder and the lens within the housing to focus the image produced by the scope onto the image sensor.

35. The combination of claim 32, in combination with the scope.

36. The combination of claim 35, in combination with the camera head.

37. The combination of claim 32, in combination with the camera head.

38. The apparatus of claim 31, in combination with the camera head.

39. The apparatus of claim 31, wherein the at least one first component is configured and arranged such that the focusing mechanism slid ably engages the at least one first component so that movement of the focusing mechanism with respect to the coupler body causes the at least one first component to move with respect to the housing, thereby causing the lens to move within the housing to focus the image produced by the scope onto the image sensor.

40. The apparatus of claim 31, wherein the focusing mechanism includes a second component, and wherein:

the at least one first component is configured and arranged such that adjustment of the focusing mechanism causes the second component to bear against the at least one first component, thereby moving the at least one first component with respect to the housing and causing the lens to move within the housing to focus the image produced by the scope onto the image sensor.

41. The apparatus of claim 40, wherein the focusing mechanism includes a focusing ring rotatably disposed on the coupler body, wherein the second component includes a finger extending from the focusing ring that rotates in a plane perpendicular to an imaging axis extending between the scope and the image sensor, and wherein:

the at least one first component includes a lens holder, having the lens disposed therein, slidingly disposed within the housing, and an outer cylinder slidingly disposed about the housing so that the outer cylinder outer cylinder is prohibited from rotating in the plane perpendicular to the imaging axis but is permitted to slide along the imaging axis, the outer cylinder being mechanically coupled to the lens holder so that sliding the outer cylinder along the imaging axis causes the lens holder to slide along the imaging axis, thereby causing the lens to move along the imaging axis to focus the image produced by the scope onto the image sensor, the outer cylinder having a ramped surface disposed at an end thereof that is angled with respect to the plane perpendicular to the imaging axis; and the finger is configured and arranged such that rotation of focusing mechanism about the coupler body causes the finger to bear against and slide along the ramped surface so that the outer cylinder slides along the imaging axis and moves the lens holder and the lens within the housing to focus the image produced by the scope onto the image sensor.

42. The apparatus of claim 31, wherein the at least one first component includes means for receiving an output from the focusing mechanism on the coupler body to move the lens within the housing to focus the image produced by the scope onto the image sensor.

43. The apparatus of claim 31, wherein each of the housing and the camera head includes a connector selected from a group consisting of a C-mount connector and a V-mount connector.

44. The apparatus of claim 43, wherein the connector of the camera head is a female connector and the connector of the housing is a male connector.

45. The apparatus of claim 31, wherein the housing includes means for mating the housing with the camera head.

46. The apparatus of claim 45, wherein the housing includes means for mating the housing with the coupler body.

47. The apparatus of claim 31, wherein the housing includes means for mating the housing with the coupler body.

48. The apparatus of claim 31, wherein the at least one first component is configured and arranged so that movement of the focusing mechanism with respect to the coupler body, while maintaining a fixed relationship between the coupler body and the housing, causes the at least one first component to be moved with respect to the at least one housing, thereby causing the lens to move within the at least one housing to focus the image produced by the scope on to the image sensor.

49. An apparatus for adapting a camera head for use in an imaging system including the camera head and a coupler positioned between the camera head and an image-producing scope, the camera head including an image sensor, the coupler including a coupler body and a focusing mechanism disposed thereon to focus an image produced by the scope onto the image sensor, the apparatus comprising:

a housing adapted to mate with the camera head;

a refractive lens movably disposed within the housing to focus an image produced by the scope onto the image sensor; and means for receiving an output from the focusing mechanism of the coupler to move the lens within the housing to focus the image produced by the scope onto the image sensor.

50. The apparatus of claim 49, in combination with the coupler.

51. The combination of claim 50, in combination with the scope.

52. The combination of claim 51, in combination with the camera head.

53. The combination of claim 50, in combination with the camera head.

54. The apparatus of claim 49, in combination with the camera head.

55. The apparatus of claim 49, wherein each of the housing and the camera head includes a connector selected from a group consisting of a C-mount connector and a V-mount connector.

56. The apparatus of claim 55, wherein the connector of the camera head is a female connector and the connector of the housing is a male connector.

57. The apparatus of claim 49, wherein the housing includes means for mating the housing with the camera head.

58. The apparatus of claim 57, wherein the housing includes means for mating the housing with the coupler body.

59. The apparatus of claim 49, wherein the housing includes means for mating the housing with the coupler body.

60. The apparatus of claim 49, wherein the means for receiving includes means for receiving the output from the focusing mechanism on the coupler body while maintaining a fixed relationship between the coupler body and the housing.

61. A method for operating an imaging system including an image-producing scope, a refractive lens, and an image sensor, the method comprising steps of:

(a) providing a coupler that is free of the refractive lens and includes a coupler body and a focusing mechanism disposed on the coupler body;

(b) disposing the refractive lens between the scope and the image sensor so that an optical axis extending between the scope and the image sensor intercepts the lens;

(c) disposing the coupler between the scope and the image sensor; and (d) moving the focusing mechanism relative to the coupler body to cause a position of the refractive lens to be adjusted to focus an image produced by the scope onto the image sensor.

62. The method of claim 61, wherein:

the method further includes a step of (e) providing an imaging unit having the image sensor and the lens disposed therein; and the step (c) includes steps of (c1) mating a first end of the coupler with the scope, and (c2) mating a second end of the coupler with the imaging unit.

63. The method of claim 62, wherein the step (e) includes steps of:
- (e1) providing a camera head including the image sensor;
- (e2) providing an adaptor including the lens; and
- (e3) mating the adaptor with the camera head to form the imaging unit.

64. The method of claim 62, wherein:
the step (a) includes a step of providing a sterile coupler;
the step (e) includes a step of providing a non-sterile imaging unit;
the step (c1) includes a step of mating the first end of the sterile coupler with a sterile scope; and
the step (c2) includes a step of mating the second end of the sterile coupler with the non-sterile imaging unit.

65. The method of claim 62, wherein the step (d) includes a step of:
- (d1) maintaining a fixed relationship between the coupler body and a body of the imaging unit when the focusing mechanism is moved relative to the coupler body to focus the image produced by the scope onto the image sensor.

66. The method of claim 65, wherein the step (d1) includes a step of:
- (d2) maintaining a fixed relationship between the scope and the body of the imaging unit when the focusing mechanism is moved relative to the coupler body to focus the image produced by the scope onto the image sensor.

67. The method of claim 62, wherein the step (d) includes a step of:
- (d1) maintaining a fixed relationship between the scope and a body of the imaging unit when the focusing mechanism is moved relative to the coupler body to focus the image produced by the scope onto the image sensor.

68. The method of claim 61, wherein the step (c) includes a step of:
- (c1) disposing the coupler between the refractive lens and the scope.

69. The method of claim 61, wherein the step (a) includes a step of:
- (a1) providing a coupler defining a light-transmissive passage between first and second ends thereof and including a light-penetrable window positioned in the passage and hermetically sealed between the first and second ends of the coupler.

70. The method of claim 61, further including a step of:
- (e) disposing of the coupler after use on only a single patient.

71. The method of claim 61, wherein the step (a) includes a step of:
- (a1) providing a coupler having a sterile drape hermetically sealed thereto.

72. The method of claim 61, wherein the step (a) includes a step:
- (a1) of providing a coupler having a sterile drape disposed thereon.

73. The method of claim 72, wherein the method further includes steps of:
- (e) providing an imaging unit having the image sensor disposed therein; and
- (f) extending the sterile drape to accommodate at least a portion of the imaging unit.

74. The method of claim 72, wherein the step (a1) includes a step of:
- (a2) providing the coupler such that the focusing, mechanism is disposed on the coupler distally of a distal end of the sterile drape.

75. The method of claim 61, wherein the step (a) includes a step of:
- (a1) providing the coupler such that a sterile drape is attached to the coupler body with an opening of the sterile drape being mounted about an outer surface of the coupler body.

76. The method of claim 61, wherein the step (a) includes a step of:
- (a1) providing a coupler defining a light-transmissive passage between first and second ends thereof with the light-transmissive passage being free of a refractive lens that intercepts the optical axis.

* * * * *